US008896311B2

(12) United States Patent
Utsumi et al.

(10) Patent No.: US 8,896,311 B2
(45) Date of Patent: Nov. 25, 2014

(54) MEASUREMENT DEVICE AND MEASUREMENT METHOD

(75) Inventors: Hideo Utsumi, Fukuoka (JP); Kazuhiro Ichikawa, Fukuoka (JP); Tetsuhiko Takahashi, Tokyo (JP)

(73) Assignee: Kyushu University, National University Corporation, Fukuoka (JP)

( * ) Notice: Subject to any disclaimer, the term of this patent is extended or adjusted under 35 U.S.C. 154(b) by 517 days.

(21) Appl. No.: 13/258,743

(22) PCT Filed: Mar. 25, 2010

(86) PCT No.: PCT/JP2010/055264
§ 371 (c)(1),
(2), (4) Date: Dec. 9, 2011

(87) PCT Pub. No.: WO2010/110384
PCT Pub. Date: Sep. 30, 2010

(65) Prior Publication Data
US 2012/0068705 A1 Mar. 22, 2012

(30) Foreign Application Priority Data
Mar. 26, 2009 (JP) .................. 2009-077389

(51) Int. Cl.
G01V 3/00 (2006.01)
A61B 5/055 (2006.01)
G01R 33/563 (2006.01)
G01R 33/60 (2006.01)
G01R 33/48 (2006.01)
G01R 33/565 (2006.01)
G01R 33/38 (2006.01)
G01R 33/44 (2006.01)

(52) U.S. Cl.
CPC ........ G01R 33/4808 (2013.01); *G01R 33/3806* (2013.01); *A61B 5/055* (2013.01); G01R 33/56383 (2013.01); G01R 33/60 (2013.01); *A61B 5/0555* (2013.01); G01R 33/56509 (2013.01); *G01R 33/445* (2013.01)
USPC ........................................ 324/321

(58) Field of Classification Search
CPC .................................... G01R 33/307
USPC ................. 324/321, 318, 307, 309
See application file for complete search history.

(56) References Cited

U.S. PATENT DOCUMENTS

| 6,538,444 | B2* | 3/2003 | Gerald et al. ................. 324/318 |
| 7,123,008 | B1* | 10/2006 | Damadian et al. ............ 324/309 |
| 8,008,917 | B2* | 8/2011 | Satragno et al. .............. 324/318 |
| 8,633,693 | B2* | 1/2014 | Bouchard et al. ............. 324/309 |
| 2002/0173715 | A1 | 11/2002 | Kruger et al. |
| 2009/0177078 | A1 | 7/2009 | Takizawa et al. |

FOREIGN PATENT DOCUMENTS

| JP | 2006-204551 | 8/2006 |
| WO | 2006/117922 | 9/2006 |
| WO | 2007/094174 | 8/2007 |

OTHER PUBLICATIONS

Supplementary European Search Report (ESR) issued Jun. 4, 2013 in European Patent Application No. EP 10 75 6180.
Peter Bornert, et al., "Principles of Whole-Body Continuously-Moving-Table MRI", Journal of Magnetic Resonance Imaging, Society for Magnetic Resonance Imaging, vol. 28, pp. 1-12, XP002544792, ISSN: 1053-1807, Jun. 25, 2008.
Kazuhiro Ichikawa et al., "Shiryo Hansogata OMRI Sochi ni Okeru Gazoka Algorithm", Abstracts of $129^{th}$ Annual Meeting of Pharmaceutical Society of Japan 4, Organizing Committee for $129^{th}$ Annual Meeting of Pharmaceutical Society of Japan, p. 138, Mar. 5, 2009.

* cited by examiner

*Primary Examiner* — Louis Arana
(74) *Attorney, Agent, or Firm* — Wenderoth, Lind & Ponack, L.L.P.

(57) ABSTRACT

A measuring instrument and a measurement method which measures, using magnetic resonance, images such as a functional image, a morphologic image of an object to be measured eliminate the influences of the moving speed of the object to be measured during moving, thereby obtaining a precise measured image. The instrument comprises: the first and second external magnetic field generation devices which generate magnetic fields for exciting the magnetic resonance of a mouse (M) as a living body to be measured; a turntable which rotates and moves the mouse (M) as an object to be measured, thereby moving the mouse (M) in the magnetic fields of the first and second external magnetic field generation devices; an OMRI measurement processing unit and an MRI measurement processing unit which obtain measured image signals within the mouse (M) by phase encoding while applying a gradient magnetic field in the moving direction (y) of the mouse (M) without stopping during the movement by the turntable; and a measured signal correction unit which corrects the measured image signal (S (k., ky)), thereby obtaining a corrected image signal (S' (k., ky)) wherein influence of movement in y-direction is corrected.

17 Claims, 6 Drawing Sheets

MEASUREMENT DEVICE AND MEASUREMENT METHOD

CROSS-REFERENCE TO RELATED APPLICATION

The present application is a continuation of International Application No. PCT/JP2010/055264 which was filed on Mar. 25, 2010, and claims priority under 35 U.S.C. §119 from Japanese Patent Application No. 2009-077389 which was filed on Mar. 26, 2009.

BACKGROUND OF THE INVENTION

1. Field of the Invention

The invention relates to a measurement device and a measurement method for obtaining images of an object, such as functional images and morphologic images, by virtue of various magnetic resonances such as electron spin resonance (ESR) and nuclear magnetic resonance (NMR).

2. Description of the Related Art

Redox metabolism containing active oxygen and free radicals is much concerned with a lot of physiological phenomena, and causes and development of diseases. Accordingly, if redox dynamics in a laboratory animal could be visualized at an individual level, it would be possible without doubt to contribute to elucidation of life phenomenon, analysis of diseases, establishment of curing diseases, and development of medicines.

Electron spin resonance imaging (ESRI), in accordance with which free radicals as intermediate products of redox metabolism are peculiarly detected, is useful for visualizing redox dynamics. However, images resulted from ESRI lack correspondence with internal organs. In order to solve this problem, there has been developed an ESRI-MRI combination type apparatus for analyzing magnetic resonance images, in which images resulted from ESRI are superimposed with MRI images of internal organs obtained by magnetic resonance imaging (MRI).

Overhauser effect is a phenomenon in which electron spin of free radicals is made to be ESR-transited to thereby cause nuclear spin to be polarized by virtue of dipole-dipole interaction between electron spin and nuclear spin. OMRI is an imaging process in which after electron spin of free radicals is excited, hydrogen nuclear spin of water molecule is polarized for carrying out MRI measurement. In OMRI, nuclear spin polarization is 330-times intensified at maximum (theoretical value) in comparison with Boltzmann distribution of usual nuclear spin. That is, OMRI makes it possible to realize 330-times sensitization (theoretical value) in comparison with usual MRI measurement.

The inventors of the present application suggested, in Japanese Patent Application Publication No. 2006-204551, the measurement device for obtaining images of organism structures by virtue of various magnetic resonances such as electron spin resonance and nuclear magnetic resonance. The measurement device is designed to include means for generating a first magnetic field having a certain intensity, means for generating a second magnetic field having an intensity greater than the intensity of the first magnetic field, means for linearly moving an object between the first magnetic field generating means and the second magnetic field generating means in synchronization with irradiation of RF pulses onto the object, and means for stopping the object to move, and obtaining images of organism structure of the object in accordance with signals detected in response to the RF pulses.

In the above-mentioned measurement device, the means for generating a first magnetic field may be employed as both an apparatus for generating an external magnetic field for ESRI and an apparatus for exciting electron spin for PEDRI (OMRI), and the means for generating a second magnetic field may be employed as an apparatus for generating an external magnetic field for MRI and OMRI. Thus, images of an amount of radicals varying with the lapse of time are obtained by OMRI, and images of radicals varying in quality are obtained by spectrum/spatial four-dimensional ESRI/MRI, and further, a magnetic field generated by the means for generating a second magnetic field can be designed to have a high intensity, resulting in that it is possible to obtain images having high sensitivity and high resolution.

In the above-mentioned measurement device, the means for linearly moving an object, disposed between the first magnetic field generating means and the second magnetic field generating means, causes the object to reciprocatingly move, and after the object is caused to stop, the measurement is carried out. Thus, high acceleration is applied to the object when the object starts moving and is stopped. Consequently, the above-mentioned measurement device is accompanied with a problem that high load is unavoidably applied to the organism as the object while moving.

Thus, the inventors are presently developing a measurement device which is able to measure an object moving between a plurality of magnetic field generating means, without stopping the object to thereby avoid the object from being loaded. However, measuring an object without stopping the object, there newly arises a problem that images of the object are influenced by a moving velocity, and resultingly, images of the object are shifted.

In view of the above-mentioned problems, it is an object of the present invention to provide a measurement device and a measurement method for obtaining images of an object to be measured such as functional images and morphologic images by virtue of magnetic resonance, both of which are capable of providing accurate images by eliminating influences caused by a moving velocity to a moving object.

A measurement device for obtaining images of an object to be measured by virtue of magnetic resonance, in accordance with the present invention, includes a magnetic field generator for generating a magnetic field to excite magnetic resonance of the object, a mover for moving one of the object and the magnetic field generator to thereby move the object in a magnetic field generated by the magnetic field generator, a measurement unit for applying a gradient magnetic field in at least one of a moving direction "y" in which the object moves relative to the magnetic field generator, and a direction "x" perpendicular to the moving direction "y" to thereby obtain image signals of the object by virtue of at least one of phase-encoding and frequency-encoding without stopping the object or the magnetic field generator while they are being moved by the mover, and a correction unit for eliminating influence on the image signals derived from movement of the object in the moving direction "y" to provide corrected image signals.

A measurement method for obtaining images of an object to be measured by virtue of magnetic resonance, in accordance with the present invention, includes moving one of the object and magnetic field generator which generates a magnetic field to excite magnetic resonance of the object to thereby move the object through a magnetic field generated by the magnetic field generator, applying a gradient magnetic field in at least one of a moving direction "y" in which the object moves relative to the magnetic field generator, and a direction "x" perpendicular to the moving direction "y" to thereby obtain image signals of the object by virtue of at least one of phase-encoding and frequency-encoding without stopping the object or the magnetic field generator while they are being moved, and eliminating influence on the image signals derived from movement of the object in the moving direction "y" to provide corrected image signals.

In accordance with the above-mentioned invention, even if the object to be measured or the magnetic field generator were moving by the mover, it would be possible to obtain corrected image signals in which the influence on the image signals derived from movement of the object relative to the magnetic field generator in the moving direction "y" is eliminated, ensuring it possible to provide accurate non-shifted images of the object, such as functional images and morphologic images.

It is preferable that the corrected image signals are obtained in accordance with the following equation:

$$S'(k_x, k_y) = \exp\left[\frac{i}{2\pi}\gamma G_y^{(n)}\left\{\frac{v_y}{2}\Delta t_y + v_y t_{y0}\right\}\Delta t_y\right] S(k_x, k_y)$$

wherein

S ($k_x$, $k_y$) indicates the image signals,

S' ($k_x$, $k_y$) indicates the corrected image signals, each of $k_x$ and $k_y$ indicates a spatial frequency in the directions "x" and "y" respectively, "γ" indicates a gyromagnetic ratio, "$G_y^{(n)}$" indicates an intensity of a gradient magnetic field of the phase-encoding or the frequency-encoding in n-th measurement, "$v_y$" indicates a moving velocity in the moving direction "y", "$\Delta t_y$" indicates a period of time during which the phase-encoding or the frequency-encoding is applied, and "$t_{y0}$" indicates a period of time until the phase-encoding or the frequency-encoding starts being applied.

Thus, it is possible to obtain the corrected image signals S' ($k_x$, $k_y$) in which the influence on the image signals derived from movement of the object in the moving direction "y", caused by a moving velocity in the moving direction "y", a period of time during which the phase-encoding or the frequency-encoding is applied, and/or a period of time until the phase-encoding or the frequency-encoding starts being applied, is eliminated, ensuring it possible to obtain accurate non-shifted images of the object, such as functional images and morphologic images, in particular, accurate two-dimensional images.

It is preferable that the corrected image signals are obtained in accordance with the following equation:

$$S'(k_x, k_y, k_z) = \exp\left[\frac{i}{2\pi}\gamma G_y^{(n)}\left\{\frac{v_y}{2}\Delta t_y + v_y t_{y0}\right\}\Delta t_y\right] S(k_x, k_y, k_z)$$

wherein

S ($k_x$, $k_y$, $k_z$) indicates the image signals,

S' ($k_x$, $k_y$, $k_z$) indicates the corrected image signals, each of $k_x$, $k_y$ and $k_z$ indicates a spatial frequency in the direction "x", the direction "y", and a direction "z", respectively, "γ" indicates a gyromagnetic ratio, "$G_y^{(n)}$" indicates an intensity of a gradient magnetic field of the phase-encoding or the frequency-encoding in n-th measurement, "$v_y$" indicates a moving velocity in the moving direction "y", "$\Delta t_y$" indicates a period of time during which the phase-encoding or the frequency-encoding is applied, and "$t_{y0}$" indicates a period of time until the phase-encoding or the frequency-encoding starts being applied.

Thus, it is possible to obtain the corrected image signals S' ($k_x$, $k_y$, $k_z$) in which the influence on the image signals derived from movement of the object in the moving direction "y", caused by a moving velocity in the moving direction "y", a period of time during which the phase-encoding or the frequency-encoding is applied, and/or a period of time until the phase-encoding or the frequency-encoding starts being applied, is eliminated, ensuring it possible to obtain accurate non-shifted images of the object, such as functional images and morphologic images, in particular, accurate three-dimensional images.

It is preferable that the magnetic field generator includes a first magnetic field generator for generating a first magnetic field having a predetermined intensity, and a second magnetic field generator for generating a second magnetic field having an intensity different from the intensity of the first magnetic field generator, and that the mover moves one of the object, the first magnetic field generator, and the second magnetic field generator to thereby move the object through magnetic fields generated by the first magnetic field generator and the second magnetic field generator in this order.

Thus, it is possible to obtain accurate non-shifted images of the object, such as functional images and morphologic images, by virtue of various magnetic resonances such as electron spin resonance and nuclear magnetic resonance, by causing a plurality of magnetic field generators to generate magnetic fields having intensities different from one another, and causing the object to pass in succession through the magnetic fields generated by the plurality of magnetic field generators.

It is preferable that the mover comprises rotating means a rotator which rotates one of the object and the first and second magnetic field generators to thereby move the object through magnetic fields generated by the first magnetic field generator and the second magnetic field generator in this order.

Thus, it is possible to obtain accurate non-shifted images of the object, such as functional images and morphologic images, by virtue of various magnetic resonances such as electron spin resonance and nuclear magnetic resonance, by causing the object or the first and second magnetic field generators to rotate, and causing the object to pass in succession through the magnetic fields generated by the plurality of magnetic field generators.

As an object to be measured in the present invention, there may be selected a body of a living (organism) or a material other than a living (for instance, semiconductor). When a living is selected as an object, there can be obtained accurate non-shifted images, such as redox dynamics images as functional images, organism functional image including metabolism images, and structural images (for instance, $^{13}C$, $^{1}H$, $^{31}P$ nuclei) as morphologic images. When a material is selected as an object, there can be obtained accurate images such as morphologic images of structures and defects, and distribution images of a compound.

It is preferable that one of the first and second magnetic field generators excites nuclear magnetic resonance for measurement, and the other excites electron spin resonance for measurement, for instance, in order to obtain images of redox dynamics. Thus, it is possible to obtain accurate non-shifted images of redox dynamics of organism by virtue of OMRI.

Any one of the first and second magnetic field generators may generate a magnetic field having a higher intensity than the other. If the second magnetic field generator is designed to generate a magnetic field having an intensity higher than the same generated by the first magnetic field generator, the first magnetic field generator generating a magnetic field having a lower intensity may be employed as an apparatus for exciting electron spin for carrying out OMRI, and the second magnetic field generator generating a magnetic field having a higher intensity may be employed as an apparatus for generating an external magnetic field for carrying out MRI and OMRI. Thus, the second magnetic field generator provides MRI images and OMRI images. In particular, in the measurement device in accordance with the present invention, since electron spin is excited by the first magnetic field generator generating a magnetic field having a lower intensity, and thereafter, OMRI measurement is carried out by the second magnetic field generator generating a magnetic field having a higher intensity, an external magnetic field used for carrying out OMRI has an extremely high intensity, and hence, it is possible to obtain accurate non-shifted OMRI images having high sensitivity and high resolution.

On the other hand, if the first magnetic field generator is designed to generate a magnetic field having an intensity higher than the same generated by the second magnetic field generator, the first magnetic field generator generating a magnetic field having a higher intensity may be employed as an apparatus for generating an external magnetic field for carrying out MRI, and the second magnetic field generator generating a magnetic field having a lower intensity may be employed as an apparatus for generating an external magnetic field for carrying out OMRI. Thus, the first magnetic field generator provides MRI images, and the second magnetic field generator provides OMRI images.

As mentioned above, since the first or second magnetic field generator excites magnetic resonance for measuring an object in the measurement device in accordance with the present invention, it is possible to obtain accurate non-shifted images of an object such as functional images and morphologic images, by virtue of various magnetic resonances such as electron spin resonance and nuclear magnetic resonance.

The present invention provides the following advantages.

(1) In accordance with the present invention, by moving an object or magnetic field generator which generates a magnetic field for exciting a magnetic resonance of the object, the object is caused to move through a magnetic field generated by the magnetic field generator, and further by applying a gradient magnetic field in a moving direction "y" in which the object moves relative to the magnetic field generator or in a direction "x" perpendicular to the moving direction "y" to thereby obtain image signals of the object by virtue of phase-encoding and/or frequency encoding without stopping the object or the magnetic field generator while they are being moved. Eliminating the influence onto the image signals caused by the movement in the direction "y" out of the thus obtained image signals, corrected image signals can be obtained. Thus, even if the object to be measured or the magnetic field generator were moving by the mover, it would be possible to obtain accurate non-shifted images of the object, such as functional images and morphologic images, in which the influence caused by a moving velocity of the moving object is eliminated.

(2) By obtaining the corrected image signals in accordance with the following equation:

$$S'(k_x, k_y) = \exp\left[\frac{i}{2\pi}\gamma G_y^{(n)}\left\{\frac{v_y}{2}\Delta t_y + v_y t_{y0}\right\}\Delta t_y\right]S(k_x, k_y)$$

it is possible to obtain accurate non-shifted images of the object, such as functional images and morphologic images, in particular, accurate two-dimensional images, in which the influence on the image signals derived from the movement of the object in the moving direction "y", caused by a moving velocity in the moving direction "y", a period of time during which the phase-encoding or the frequency-encoding is applied, and/or a period of time until the phase-encoding or the frequency-encoding starts being applied, is eliminated.

(3) By obtaining the corrected image signals in accordance with the following equation:

$$S'(k_x, k_y, k_z) = \exp\left[\frac{i}{2\pi}\gamma G_y^{(n)}\left\{\frac{v_y}{2}\Delta t_y + v_y t_{y0}\right\}\Delta t_y\right]S(k_x, k_y, k_z)$$

it is possible to obtain accurate non-shifted images of the object, such as functional images and morphologic images, in particular, accurate three-dimensional images, in which the influence on the image signals derived from the movement of the object in the moving direction "y", caused by a moving velocity in the moving direction "y", a period of time during which the phase-encoding or the frequency-encoding is applied, and/or a period of time until the phase-encoding or the frequency-encoding starts being applied, is eliminated.

(4) By designing the magnetic field generator to include a first magnetic field generator for generating a first magnetic field having a predetermined intensity, and a second magnetic field generator for generating a second magnetic field having an intensity different from the intensity of the first magnetic field generator, and further by designing the mover to move the object or the first and second magnetic field generators to thereby move the object through magnetic fields generated by the first and second magnetic field generators in this order, it is possible to obtain, without stopping the object to move, accurate non-shifted images of the object, such as functional images and morphologic images, by virtue of various magnetic resonances such as electron spin resonance and nuclear magnetic resonance.

(5) By designing the mover to comprise a rotator which rotates one of the object and the first and second magnetic field generators to thereby move the object through magnetic fields generated by the first magnetic field generator and the second magnetic field generator in this order, it is no longer necessary to reciprocatingly move the object, and it is possible to obtain accurate non-shifted images of the object, such as functional images and morphologic images, by virtue of various magnetic resonances such as electron spin resonance and nuclear magnetic resonance, without stopping the object or the first and second magnetic field generators and further with the object being moved in rotation. Thus, it is possible to eliminate a load exerted on the object, caused when the object is temporarily stopped in reciprocal movement during measurement carried out in a conventional manner, and further, possible to avoid the first and second magnetic field generators from being loaded when they are caused to stop.

(6) By designing one of the first and second magnetic field generators to excite nuclear magnetic resonance, and the other to excite electron spin resonance, it is possible to obtain accurate non-shifted redox dynamics images of organism by virtue of OMRI.

(7) If the second magnetic field generator is designed to generate a magnetic field having an intensity higher than the same generated by the first magnetic field generator, the first magnetic field generator generating a magnetic field having a lower intensity may be employed as an apparatus for exciting electron spin for carrying out OMRI, and the second magnetic field generator generating a magnetic field having a higher intensity may be employed as an apparatus for generating an external magnetic field for carrying out MRI and OMRI. Thus, an external magnetic field used for carrying out OMRI has an extremely high intensity, and hence, it is possible to obtain accurate non-shifted OMRI images having high sensitivity and high resolution.

(8) If the first magnetic field generator is designed to generate a magnetic field having an intensity higher than the same generated by the second magnetic field generator, the first magnetic field generator generating a magnetic field having a higher intensity may be employed as an apparatus for generating an external magnetic field for carrying out MRI, and the second magnetic field generator generating a magnetic field having a lower intensity may be employed as an apparatus for generating an external magnetic field for carrying out OMRI. Thus, it is possible to obtain accurate non-shifted OMRI images having high sensitivity.

The above and other objects and advantageous features of the present invention will be made apparent from the following description made with reference to the accompanying drawings, in which like reference characters designate the same or similar parts throughout the drawings.

DESCRIPTION OF THE EXEMPLARY EMBODIMENT

Figure 1:
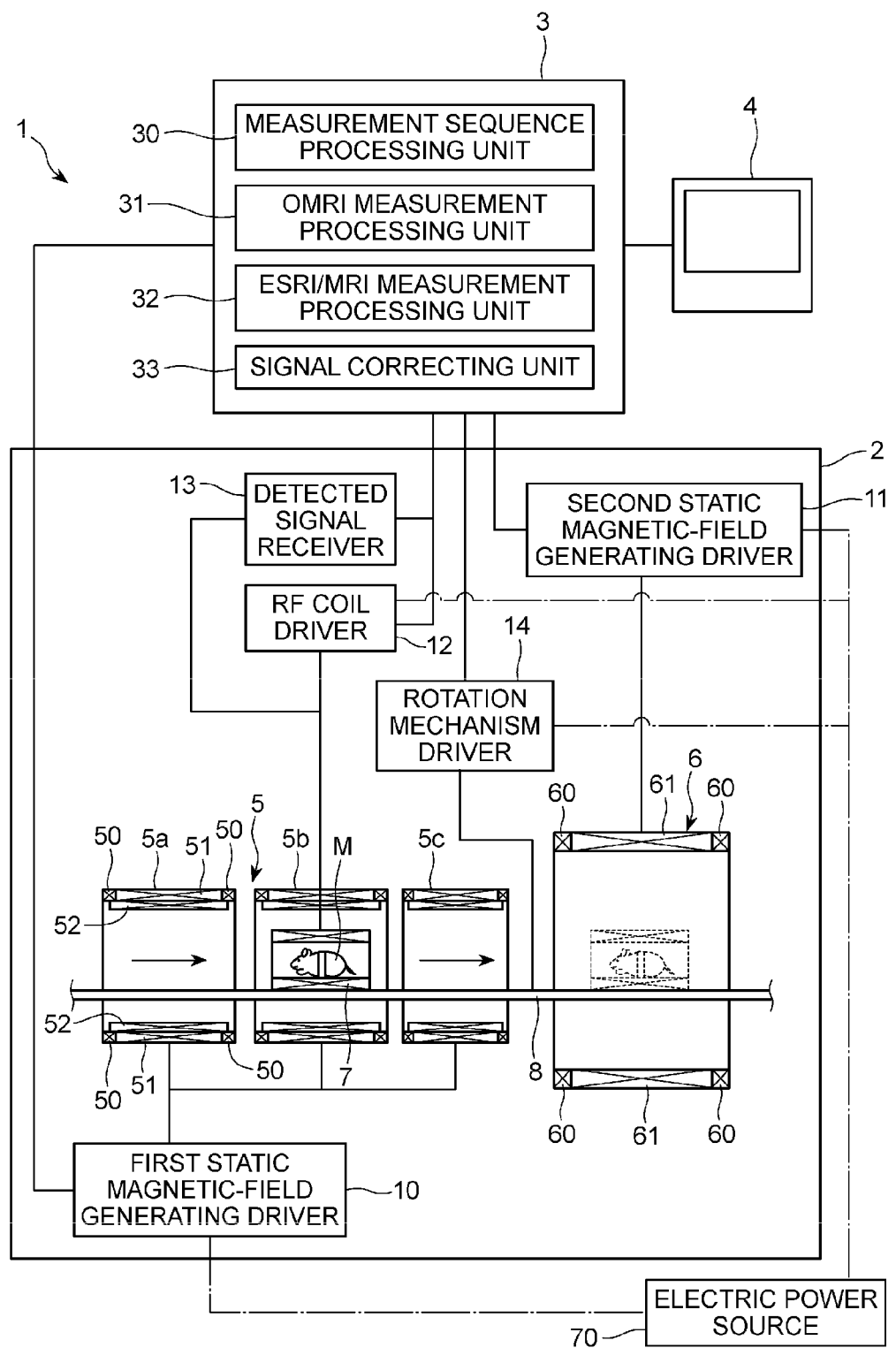
FIG. 1 is a view illustrating a structure of the measurement device in accordance with the embodiment of the present invention.
Figure 2:
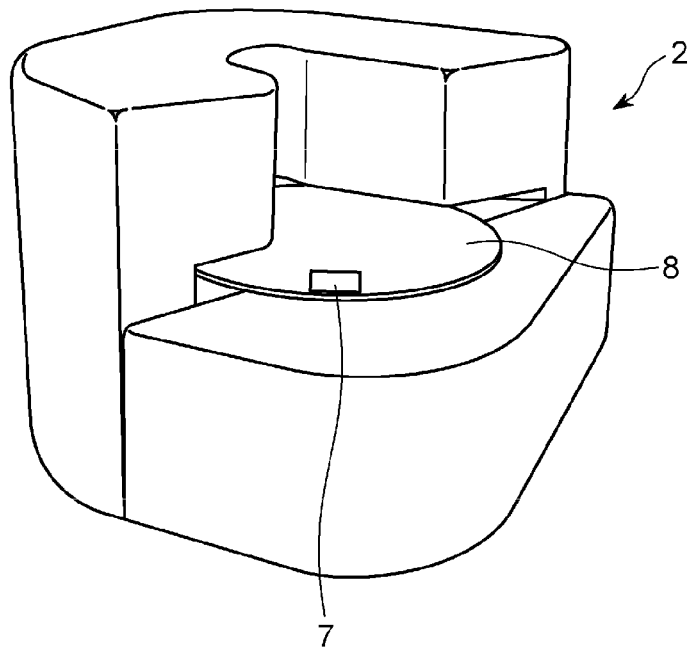
FIG. 2 is a perspective view of a main unit of the measurement device illustrated in FIG. 1.
Figure 3:
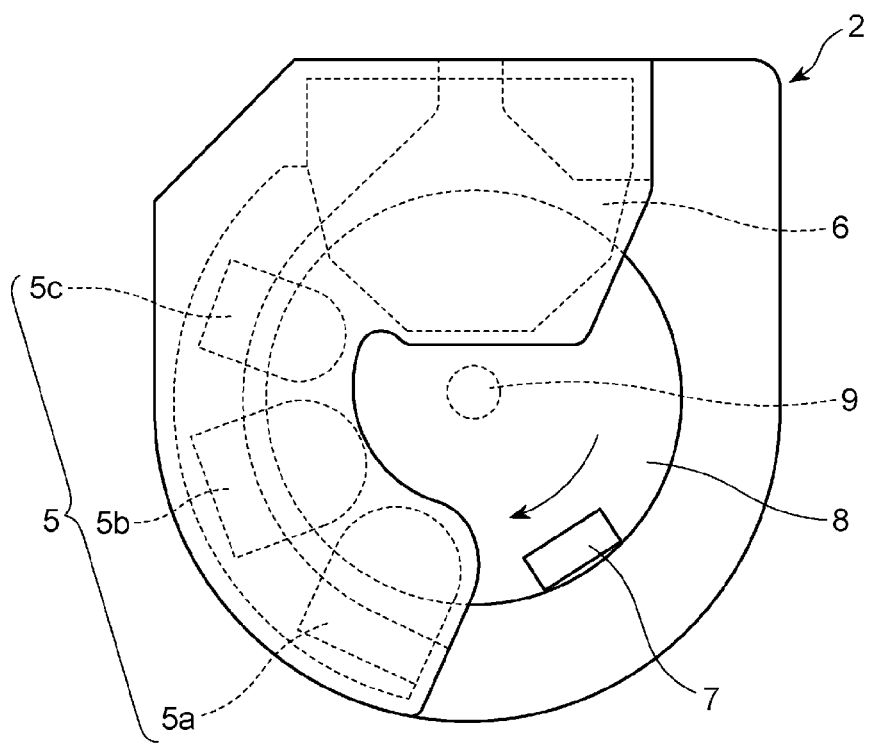
FIG. 3 is a plan view of a main unit of the measurement device illustrated in FIG. 1.

FIG. 1 is a view illustrating a structure of a measurement device in accordance with the exemplary embodiment of the present invention, FIG. 2 is a perspective view of a main unit of the measurement device illustrated in FIG. 1, and FIG. 3 is a plan view of the main unit.

With reference to FIG. 1, the measurement device 1 in accordance with the embodiment of the present invention measures an organism as an object, and includes a main unit 2 in which an organism as an object (a mouse M in the drawings) is put, and which measures the object, a control unit 3 controlling operation of each component of the main unit 2, and a display unit 4 displaying results of processing carried out by the control unit 3.

The main unit 2 includes an apparatus 5 for generating a first external magnetic field having a low intensity, as the first magnetic field generator for generating a first magnetic field, an apparatus 6 for generating a second external magnetic field having a high intensity, as the second magnetic field generator for generating a second magnetic field, a cylindrical RF coil (a resonator) 7, a turntable 8 rotating around a vertical axis, as the rotator, a driver 10 for generating a first static magnetic field, a driver 11 for generating a second static magnetic field, a RF coil driver 12, a detected signal receiver 13, and a driver 14 for driving a rotation mechanism (mentioned later). The turntable 8 is rotated by a mechanism 9 for rotating an object (see FIG. 3), including a motor, a pulley, and a belt and so on.

The RF coil 7 is fixed on a periphery of the turntable 8. An organism as an object to be measured is kept in the RF coil 7, and is rotated together with the turntable 8 to thereby pass through magnetic fields in an order, generated by the first external magnetic field generating apparatus 5 and the second external magnetic field generating apparatus 6. In an example illustrated in FIG. 3, the turntable 8 rotates in a clockwise direction. The RF coil 7 generates an electromagnetic radiation magnetic field in a direction perpendicular to static magnetic fields generated by the first external magnetic field generating apparatus 5 and the second external magnetic field generating apparatus 6.

The first external magnetic field generating apparatus 5 in the embodiment is comprised of three external magnetic field generating apparatuses 5a, 5b and 5c, each of which includes an eternal magnet 50, a gradient magnetic field coil 51, and a magnetic field sweeping coil 52. The first external magnetic field generating apparatus 5 provides an excited magnetic field for OMRI in a space in which the RF coil 7 fixed on the turntable 8 passes. The first external magnetic field generating apparatus 5 excites electron spins of free radicals in an organism as an object kept in the RF coil 7 for carrying out OMRI measurement in the second external magnetic field generating apparatus 6.

The second external magnetic field generating apparatus 6 includes an eternal magnet 60 for generating a static magnetic field in a space in which the RF coil 7 fixed on the turntable 8 passes, and further includes a gradient magnetic field coil 61 which generates gradient magnetic fields having a certain intensity at predetermined times in the static magnetic field generated by the eternal magnet 60, in accordance with a predetermined MR pulse sequence. The second external magnetic field generating apparatus 6 provides an external magnetic field for carrying out MRI/OMRI. In the second external magnetic field generating apparatus 6, MRI measurement and OMRI measurement are carried out.

The first external magnetic field generating apparatus 5 is electrically connected to the control unit 3 through the driver 10 which generates a first static magnetic field. The first static magnetic field generating driver 10 is electrically connected to an electric power source 70 for providing electric power to the gradient magnetic field coil 51 and the magnetic field sweeping coil 52. The first static magnetic field generating driver 10 controls the gradient magnetic field coil 51 and the magnetic field sweeping coil 52 in accordance with instructions received from the control unit 3. The first external magnetic field generating apparatus 5 in the present embodiment generates a magnetic field having an intensity of 20 mT. It should be noted that the intensity may be varied such that it is greater than 0, but equal to or smaller than 50 mT in OMRI, and that it is greater than 0, but equal to or smaller than 11 mT in MRI. Furthermore, the eternal magnet 60 may be replaced with an electromagnet.

The second external magnetic field generating apparatus 6 is electrically connected to the control unit 3 through the driver 11 which generates a second static magnetic field. The second static magnetic field generating driver 11 is electrically connected to the electric power source 70 for providing electric power to the gradient magnetic field coil 61. The second static magnetic field generating driver 11 controls the gradient magnetic field coil 61 in accordance with instructions received from the control unit 3. The second external magnetic field generating apparatus 6 in the present embodiment generates a magnetic field having an intensity of 1.5 T. It should be noted that the intensity may be varied such that it is greater than 0, but equal to or smaller than 11 T. It is more preferable for the magnetic field to have a greater intensity. In the present embodiment, there is used the eternal magnet 60, which is capable of intensifying an intensity of the magnetic field up to about 2 T. As an alternative, the eternal magnet 60 may be replaced with a superconducting magnet, in which case, an intensity of the magnetic field can be intensified up to about 11 T.

The RF coil 7 is electrically connected to the control unit 3 through the RF coil driver 12 or the detected signal receiver 13. The rotation mechanism 9 illustrated in FIG. 3 is electrically connected to the control unit 3 through the driver 14 which drives the rotation mechanism 9. The RF coil driver 12 and the driver 14 are electrically connected to the electric power source 70 for providing electric power to the RF coil 7 and the rotation mechanism 9.

The RF coil driver 12 and the driver 14 drive the RF coil 7 and the rotation mechanism 9, respectively, in accordance with a sequence received from the control unit 3. The RF coil driver 12 drives the RF coil 7 in synchronization with the driver 14 at a timing at which the RF coil 7 rotating together with the turntable 8 passes magnetic fields generated by the first external magnetic field generating apparatus 5 and the second external magnetic field generating apparatus 6. Applying a high-frequency pulse to the RF coil 7, a high-frequency magnetic field is generated in the RF coil 7, and accordingly, the organism as an object put in the RF coil 7 is exposed to the high-frequency magnetic field.

Electron spin resonance signals received at the RF coil 7 in the first external magnetic field generating apparatus 5 and magnetic resonance signals received at the RF coil 7 in the second external magnetic field generating apparatus 6 are transferred to the detected signal receiver 13, and then, transferred to the control unit 3. It is preferable that a period of time for driving the first external magnetic field generating apparatus 5 and then the second external magnetic field generating apparatus 6 is equal to or smaller than 1 second, and it is more preferable that the period of time is equal to or smaller than 0.7 seconds. In the present embodiment, the period of time is set equal to 0.5 seconds.

The control unit 3 includes a measurement sequence processing unit 30 for obtaining an electron spin resonance signal and a magnetic resonance signal of the organism as an object in accordance with a measurement sequence, a unit 31 for processing OMRI measurement, a unit 32 for processing MRI measurement, and a unit 33 for correcting signals. The measurement sequence processing unit 30 includes a sequence used for providing electric power to the first external magnetic field generating apparatus 5, the second external magnetic field generating apparatus 6, the RF coil 7, and the rotation mechanism 9, and a sequence for carrying out measurement in the RF coil 7. The measurement sequence processing unit 30 controls the first external magnetic field generating apparatus 5, the second external magnetic field generating apparatus 6, the RF coil 7, and the rotation mechanism 9. The control unit 3 is actually comprised of a computer system, and executes a computer program stored in a recording medium such as a hard disc to thereby carry out the above-mentioned functions.

The OMRI measurement processing unit 31 and the MRI measurement processing unit 32 process images in accordance with electron spin resonance signals and magnetic resonance signals obtained in accordance with the measurement sequence to thereby provide measured image signals. The signal correcting unit 33 corrects image signals obtained through the OMRI measurement processing unit 31 and the MRI measurement processing unit 32 to thereby provide corrected image signals in which the influence caused by movement of the object is eliminated. The corrected image signals corrected by the signal correcting unit 33 are displayed on the display unit 4.

Hereinbelow is explained in detail the process of correcting the image signals, carried out by the signal correcting unit 33.

The OMRI measurement processing unit 31 and the MRI measurement processing unit 32 apply a gradient magnetic field in a moving direction "y" in which the organism as an object moves relative to the first and second external magnetic field generating apparatuses 5 and 6, and/or a direction "x" perpendicular to the moving direction "y" to thereby obtain image signals of the organism as an object by virtue of phase-encoding and/or frequency-encoding without a pause while the turntable 8 is rotating.

Hereinbelow is explained a case, for simplification, that a gradient magnetic field is applied in a direction "x" perpendicular to the moving direction "y" to thereby obtain image signals of the organism as an object by virtue of phase-encoding. However, it should be noted that frequency-encoding may be used in place of or together with phase-encoding. A direction in which a gradient magnetic field is applied may be changed into another direction.

Figure 4:
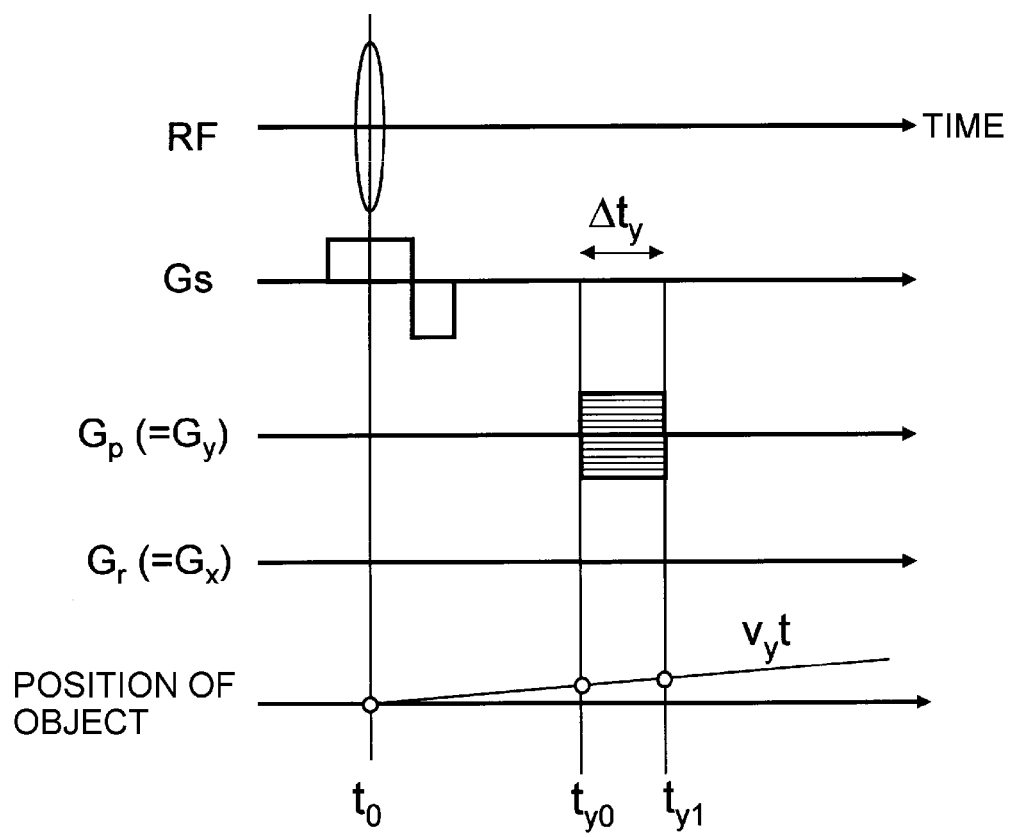
FIG. 4 shows an example of the measurement sequence.
Figure 5:
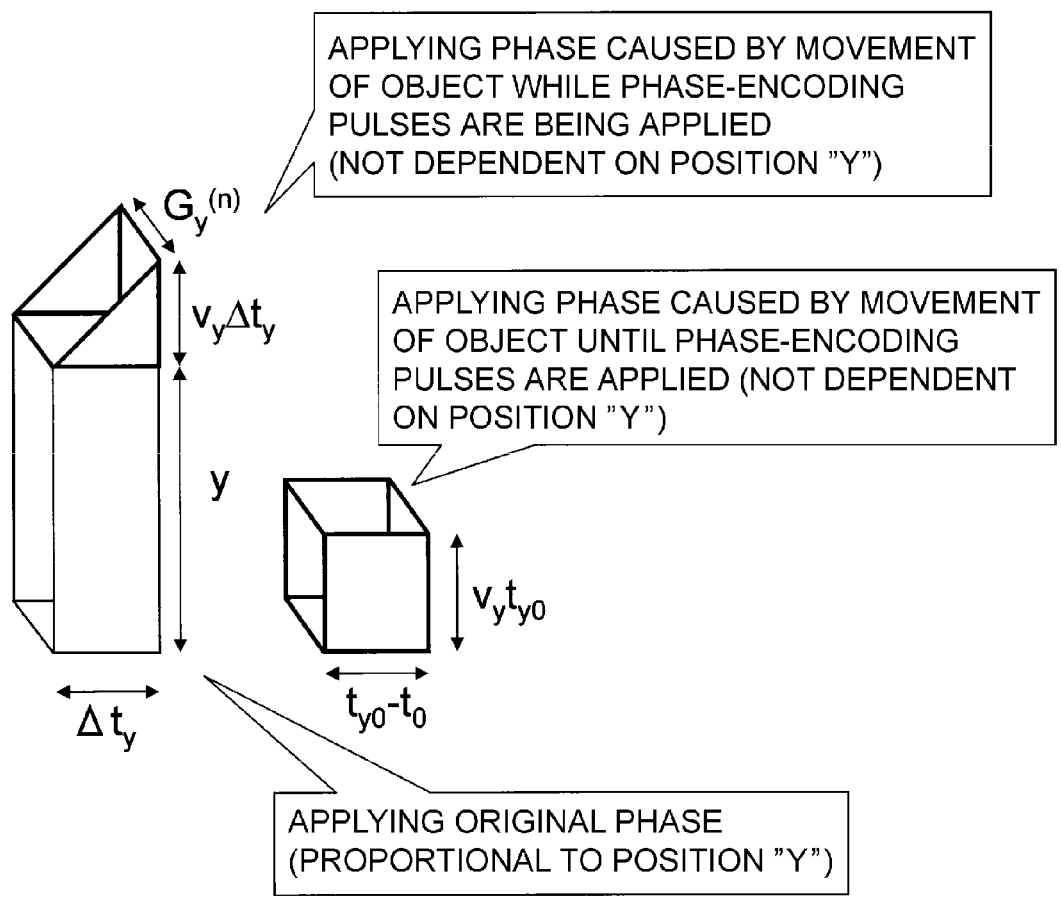
FIG. 5 is a typical view showing an intensity of a gradient magnetic field $G_y^{(n)}$ of phase-encoding applied to an organism as an object in the case that the measurement is carried out in accordance with the measurement sequence illustrated in FIG. 4.

FIG. 4 illustrates a measurement sequence in which a gradient magnetic field is applied in a direction "x" perpendicular to the moving direction "y" to thereby obtain image signals of the organism as an object by virtue of phase-encoding. As illustrated in FIG. 4, in the measurement sequence, a gradient magnetic field Gs is applied simultaneously ($t_0$) with application of a RF pulse, and then, a phase-encoding pulse Gp during $t_{y0}$ $t_{y1}$ to obtain image signals. FIG. 5 is a typical view showing an intensity of a gradient magnetic field $G_y^{(n)}$ of phase-encoding applied to the organism as an object in the case that the measurement is carried out in accordance with the measurement sequence illustrated in FIG. 4. "$v_y$" indicates a moving velocity of the organism in the moving direction "y". Since the organism does move in the direction "x", "$v_{xs}$" is zero. The superscript (n) indicates that "$G_y$" increases at every measurement (scan).

The magnetized signal $S(k_x, k_y)$ encoded by the gradient magnetic field is expressed as follows:

$$S(k_x,k_y)=\int_{dx,dy}\rho(x,y)\exp[-i(k_xx+k_yy)]dxdy \quad (1)$$

Herein, each of "kx" and "ky" indicates a spatial frequency, and "$\rho(x, y)$" indicates a magnetization density.

A location of the organism as an object while moving is expressed as follows:

$$k_xx = \frac{1}{2\pi}\int_{\tau=0}^{\tau=tx}\gamma G_x(x)d\tau \quad (2\text{-}1)$$

$$k_yy = \frac{1}{2\pi}\int_{\tau=0}^{\tau=ty}\gamma G_y^{(n)}(y)d\tau \quad (2\text{-}2)$$

Herein, "$\gamma$" indicates a gyromagnetic ratio, and "$\tau$" indicates a period of time.

Since the object moves only in the "y" direction, and the gradient magnetic field $G_y^{(n)}$ is applied only during $t_{y0}$ to $t_{y1}$, the above-mentioned equation (2-2) is expressed as follows:

$$k_y y = \frac{1}{2\pi} \gamma G_y^{(n)} \left[ y\tau + \frac{v_y}{2} \tau^2 \right]_{\tau=t_{y0}}^{\tau=t_{y1}} \quad (2\text{-}3)$$

$$= \frac{1}{2\pi} \gamma G_y^{(n)} \left[ \left\{ y + \frac{v_y}{2} \Delta t_y + v_y t_{y0} \right\} \Delta t_y \right]$$

Thus, the above-mentioned equation (1) is expressed as follows:

$$S(k_x, k_y) = \qquad (3)$$
$$\int_{dx,dy} \rho(x,y) \exp\left[ -\frac{i}{2\pi} k_x x - \frac{i}{2\pi} \gamma G_y^{(n)} \left\{ y + \frac{v_y}{2} \Delta t_y + v_y t_{y0} \right\} \Delta t_y \right] dx\, dy$$

Herein, introducing "y'" defined with the equation (4), there is carried out coordinate transformation.

$$y' = y + \frac{v_y}{2} \Delta t_y + v_y t_{y0}, \; dy' = dy \qquad (4)$$

By carrying out the coordinate transformation, "y" is expressed with the equation (5).

$$y = y' - \frac{v_y}{2} \Delta t_y - v_y t_{y0} \qquad (5)$$

Carrying out coordinate transformation by introducing the equation (5) into the equation (3), there is obtained the equation (6).

$$S(k_x, k_y) = \qquad (6)$$
$$\int_{dx,dy'} \rho\left(x, \left(y' - \frac{v_y}{2} \Delta t_y - v_y t_{y0}\right)\right) \exp\left[ -\frac{i}{2\pi} (k_x x + \gamma G_y^{(n)} t_y y') \right] dx\, dy'$$

By carrying out Fourier transformation, the equation (6) is expressed as follows:

$$F^{-1}\{S(k_x, k_y)\} = F^{-1}\left\{ \int_{dx,dy'} \rho\left(x, \left(y' - \frac{v_y}{2} \Delta t_y - v_y t_{y0}\right)\right) \right. \qquad (7)$$
$$\left. \exp\left[ -\frac{i}{2\pi}(k_x x + \gamma G_y^{(n)} t_y y') \right] dx\, dy' \right\}$$

$$= \rho\left(x, \left(y' - \frac{v_y}{2} \Delta t_y - v_y t_{y0}\right)\right) \qquad (8)$$

The equation (8) indicates that the movement of the organism as an object in a direction "y" is expressed as movement in a direction "y" in the measured images. An example of calculated lengths by which the object is shifted in the actually measured images is shown in Table 1. Parameters necessary for calculating the lengths are a moving velocity "$v_y$" in a direction "y", a period of time "$\Delta t_y$" during which phase-encoding is applied, and a period of time "$t_{y0}$" until the phase-encoding starts being applied. As is understood in Table 1, shifting lengths (calculated lengths) calculated in accordance with the equation (8) are almost coincident with actually measured lengths.

TABLE 1

| $v_y$ (m/s) | shifting length (calculated) [mm] | shifting length (experiment) [mm] |
|---|---|---|
| 0.5 | 3.04 | 3.04 |
| 1.0 | 6.07 | 5.67 |
| 1.5 | 9.11 | 9.17 |
| 2.0 | 12.1 | 12.1 |

Then, when the influence caused by the movement in the direction "y" is eliminated, since the equation (3) can be rewritten into the equation (9), the corrected image signal is expressed as shown in the equation (10).

$$S(k_x, k_y) = \exp\left[ -\frac{i}{2\pi} \gamma G_y^{(n)} \left\{ \frac{v_y}{2} \Delta t_y + v_y t_{y0} \right\} \Delta t_y \right] \times \qquad (9)$$
$$\int_{dx,dy} \rho(x,y) \exp\left[ -\frac{i}{2\pi} k_x x - \frac{i}{2\pi} \gamma G_y^{(n)} \Delta t_y y \right] dx\, dy$$

$$S'(k_x, k_y) = \exp\left[ \frac{i}{2\pi} \gamma G_y^{(n)} \left\{ \frac{v_y}{2} \Delta t_y + v_y t_{y0} \right\} \Delta t_y \right] S(k_x, k_y) \qquad (10)$$

The signal correcting unit 33 calculates the corrected image signals S' ($k_x, k_y$) in accordance with the equation (10), based on the measured image signals S ($k_x, k_y$). This calculation corresponds to carrying out phase rotation.

By applying Fourier transformation to the corrected image signals S' ($k_x, k_y$), there is obtained the equation (11).

$$F^{-1}\{S'(k_x, k_y)\} = F^{-1}\left\{ \int_{dx,dy} \rho(x,y) \exp \right. \qquad (11)$$
$$\left. \left[ \frac{i}{2\pi} \gamma G_y^{(n)} \left\{ \frac{v_y}{2} \Delta t_y + v_y t_{y0} \right\} \Delta t_y \right] dx\, dy \right\}$$
$$= F^{-1}\left\{ \int_{dx,dy} \rho(x,y) \exp \right.$$
$$\left. \left[ -\frac{i}{2\pi}(k_x x + \gamma G_y^{(n)} t_y y) \right] dx\, dy \right\}$$
$$= \rho(x,y)$$

Thus, it is understood that it is possible to obtain accurate images in which the influence caused by the "y" direction movement is eliminated, by applying Fourier transformation to the corrected image signals S' ($k_x, k_y$).

Hereinbelow is explained the operation of the measurement device 1 having the above-mentioned structure.

First, a small animal as an organism or an object, for instance, a mouse M is put in the RF coil 7 fixed on the turntable 8. In the present embodiment, redox metabolism abnormality in oxidization stress disease in the organism, or brain functions in schizophrenia is analyzed with spatial images.

Then, the rotation mechanism 9 is driven to rotate the turntable 8 to cause the mouse M to pass through magnetic fields generated by the first external magnetic field generating apparatus 5 and the second external magnetic field generating apparatus 6 in this order. The first external magnetic field generating apparatus 5 irradiates high-frequency waves through the RF coil 7 and drives the magnetic field sweeping coil 52 to thereby swiftly sweep a static magnetic field. Thus, unpaired electron in the mouse M absorbs the high-frequency waves, and hence, electron spins are excited in resonance.

Having passed through the first external magnetic field generating apparatus 5, the mouse M enters the second external magnetic field generating apparatus 6, and thus, is put in a highly intensive static magnetic field having an intensity of 1 T or greater, in the present embodiment, 1.5 T. As a result, electron spins having been excited in resonance in the first external magnetic field generating apparatus 5 are transited in energy into nuclear spins. Then, signals generated from the mouse M as a result of the irradiation of high-frequency waves through the RF coil 7 are received at the detected signal receiver 13.

The signals received at the detected signal receiver 13 in the above-mentioned manner are transferred to the control unit 3, and then, processed in the OMRI measurement processing unit 31 and the MRI measurement processing unit 32. The MRI measurement processing unit 32 processes the signals having been obtained through the RF coil 7 in the first external magnetic field generating apparatus 5, to thereby synthesize MRI images. The OMRI measurement processing unit 31 processes the signals having been obtained through the second external magnetic field generating apparatus 6 to thereby synthesize images showing nuclear spin distribution.

The image signals obtained through the MRI measurement processing unit 32 and the OMRI measurement processing unit 31 are corrected by the above-mentioned signal correcting unit 33, and the corrected image signals obtained by the signal correcting unit 33 are displayed on the display unit 4.

As mentioned above, in the measurement device 1 in accordance with the present embodiment, the MRI measurement processing unit 32 and the OMRI measurement processing unit 31 provide the image signals S ($k_x$, $k_y$), and the image signals are corrected into the corrected image signals S' ($k_x$, $k_y$) in which the influence caused by the "y" direction movement is eliminated. Hence, even if the mouse M were moving by the turntable 8, it is possible to obtain accurate non-shifted MRI images and OMRI images of the mouse M in which the influence caused by the moving velocity of the moving mouse M is eliminated.

In the measurement device 1 in accordance with the present embodiment, the first external magnetic field generating apparatus 5 and the second external magnetic field generating apparatus 6 may be designed to generate a magnetic field having an intensity different from each other, in which case, it is possible to rotate the turntable 8 together with the mouse M to cause the mouse M to pass successively through magnetic fields generated by the first and second external magnetic field generating apparatuses 5 and 6, to thereby obtain accurate non-shifted MRI images and OMRI images of the mouse M. Consequently, it is no longer necessary to reciprocatingly move the mouse M unlike the conventional process, and hence, it is possible to avoid the mouse from being loaded during moving and when stopped.

In the measurement device 1, the first external magnetic field generating apparatus 5 generating a magnetic field having a lower intensity is employed as an apparatus for exciting electron spin for carrying out OMRI, and the second external magnetic field generating apparatus 6 generating a magnetic field having a higher intensity is employed as an apparatus for generating an external magnetic field for carrying out MRI and OMRI. Accordingly, in the measurement device 1, since electron spin is excited by the first external magnetic field generating apparatus 5 generating a magnetic field having a lower intensity, and thereafter, OMRI measurement is carried out by the second external magnetic field generating apparatus 6 generating a magnetic field having a higher intensity, an external magnetic field used for carrying out OMRI has an extremely high intensity, and hence, it is possible to obtain accurate non-shifted OMRI images having high sensitivity and high resolution.

In the measurement device 1, it is possible to carry out the measurement by rotating the turntable 8 in a reverse direction to thereby cause the mouse M to pass through the second external magnetic field generating apparatus 6 and the first external magnetic field generating apparatus 5 in this order, in which case, the second external magnetic field generating apparatus 6 generating a magnetic field having a higher intensity may be employed as an apparatus for generating an external magnetic field for carrying out MRI, and the first external magnetic field generating apparatus 5 generating a magnetic field having a lower intensity may be employed as an apparatus for generating an external magnetic field for carrying out OMRI.

Thus, the second external magnetic field generating apparatus 6 provides MRI images, and the first external magnetic field generating apparatus 5 provides OMRI images.

The measurement device 1 in accordance with the present embodiment is designed to rotate the mouse M by means of the turntable 8. As an alternative, the first and second external magnetic field generating apparatuses 5 and 6 may be designed to rotate without rotating the mouse M, in which case, the mouse M may be caused to make reciprocating movement. Since the moving direction "y" of the mouse M relative to the first and second external magnetic field generating apparatuses 5 and 6 is kept unchanged, it is possible to correct the image signals through the signal correcting unit 33 in accordance with the above-mentioned way.

In the above-mentioned case, since the mouse M is kept stationary, it is possible to avoid the mouse M from feeling uncomfortable while the measurement is being carried out, accomplishing the measurement device friendly with the organism. In addition, since it is not necessary in the measurement device 1 in accordance with the present embodiment to cause the first and second external magnetic field generating apparatuses 5 and 6 to make reciprocating movement, no load is applied to the mouse M due to the movement of the first and second external magnetic field generating apparatuses 5 and 6 when they move and stop.

The measurement device 1 in accordance with the present embodiment is designed to include the two external external magnetic field generating apparatuses used for carrying out MRI/OMRI measurement, but may be designed to include two or more external external magnetic field generating apparatuses which generate magnetic fields each having an intensity different from one another, and through which the organism as an object is caused to move. The signal correcting unit 33 in the measurement device 1 in accordance with the present embodiment may be designed to correct the image signals even when the organism as an object is caused to move within a single external magnetic field generating apparatus.

In the measurement device 1 in accordance with the present embodiment, various measuring devices such as an X-ray CT (Computed Tomography) apparatus, a supersonic-wave visualizing apparatus and a positron emission tomography (PET) apparatus may be arranged on a path on which the organism as an object situated on the turntable 8 is rotated, to thereby successively make a plurality of measurements.

The measurement device 1 can provide structural images as morphologic images as well as redox dynamics images as functional images of an organism. In addition, the measurement device can provide morphologic images of a material other than an organism, for instance, a structure and/or a defect of semiconductor. The measurement device can provide images of an object, such as functional images and morphologic images, by virtue of various resonances such as electron spin resonance and nuclear magnetic resonance.

The signal correcting unit 33 in the measurement device 1 in accordance with the present embodiment is designed to correct two-dimensional images such as MRI/OMRI images. It should be noted that the correction process carried out in the signal correcting unit 33 may be applied to three- or more-dimensional images.

Figure 6:
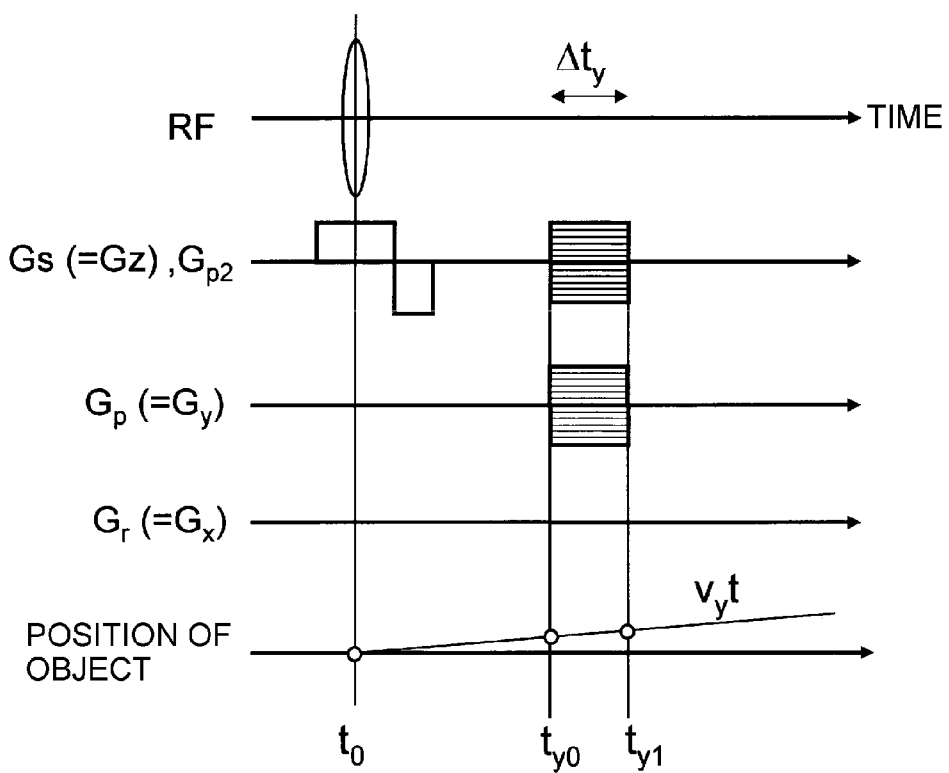
FIG. 6 shows another example of the measurement sequence.
Figure 7:
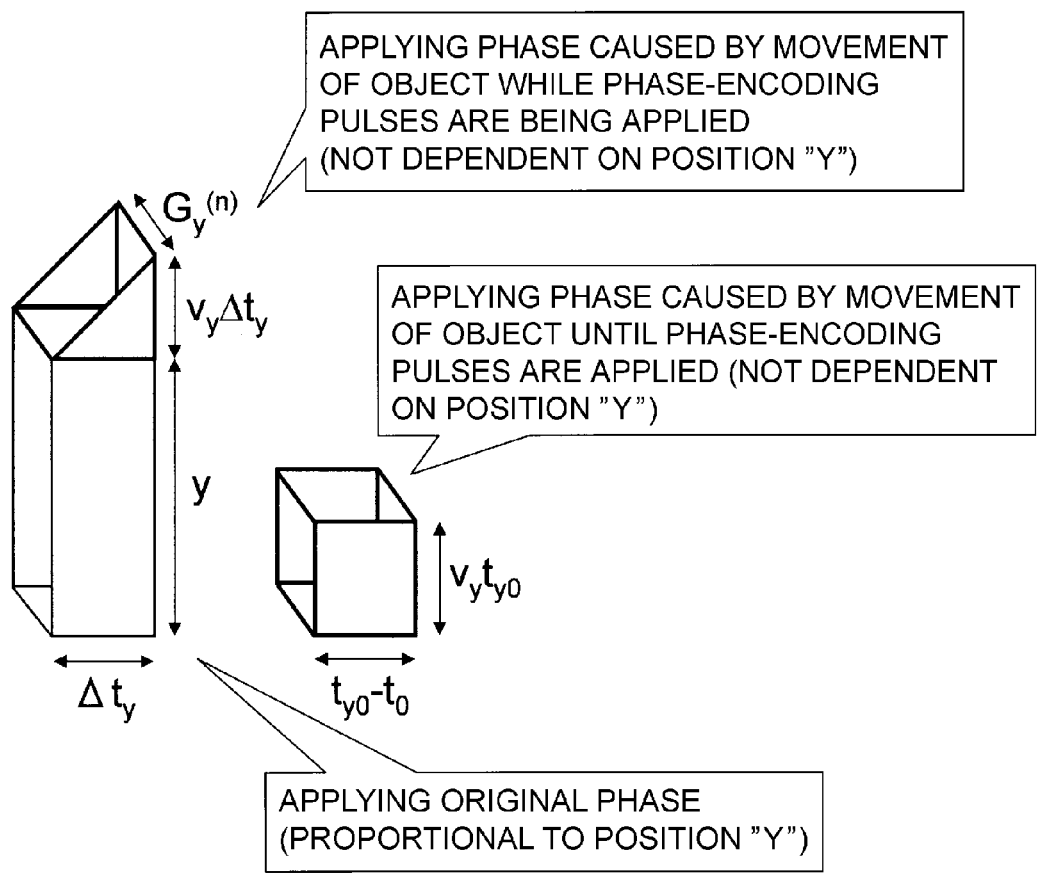
FIG. 7 is a typical view showing an intensity of a gradient magnetic field $G_y^{(n)}$ obtained when phase-encoding is applied to an organism as an object in the case that the measurement is carried out in accordance with the measurement sequence illustrated in FIG. 6.

FIG. 6 illustrates a measurement sequence in which a gradient magnetic field is applied in directions "x" and "z" both perpendicular to the moving direction "y" to thereby obtain image signals of the organism as an object by virtue of phase-encoding. As illustrated in FIG. 6, in the measurement sequence, a gradient magnetic field Gs is applied simultaneously with application of a RF pulse ($t_0$), and then, phase-encoding pulses $G_p$ and $G_{p2}$ during $t_{y0}$ to $t_{y1}$ to obtain image signals. FIG. 7 is a typical view showing an intensity of a gradient magnetic field $G_y^{(n)}$ of phase-encoding applied to the organism as an object in the case that the measurement is carried out in accordance with the measurement sequence. "$v_y$" indicates a moving velocity of the organism in the moving direction "y".

The above-mentioned equations (1) to (11) are expressed with the corresponding equations (12) to (22) indicated below.

$$S(k_x, k_y, k_z) = \int_{dx,dy,dz} \rho(x, y, z)\exp[-i(k_x x + k_y y + k_z z)]dx\,dy\,dz \quad (12)$$

$$k_x x = \frac{1}{2\pi}\int_{\tau=0}^{\tau=tx} \gamma G_x(x)d\tau \quad (13\text{-}1)$$

$$k_y y = \frac{1}{2\pi}\int_{\tau=0}^{\tau=ty} \gamma G_y^{(n)}(y)d\tau \quad (13\text{-}2)$$

$$k_z z = \frac{1}{2\pi}\int_{\tau=0}^{\tau=tz} \gamma G_z^{(n)}(z)d\tau \quad (13\text{-}3)$$

$$k_y y = \frac{1}{2\pi}\gamma G_y^{(n)}\left[y\tau + \frac{v_y}{2}\tau^2\right]_{\tau=ty0}^{\tau=ty1} \quad (13\text{-}4)$$

$$= \frac{1}{2\pi}\gamma G_y^{(n)}\left[\left\{y + \frac{v_y}{2}\Delta t_y + v_y t_{y0}\right\}\Delta t_y\right]$$

$$k_z z = \frac{1}{2\pi}\gamma G_z^{(n)}[y\tau]_{\tau=tz0}^{\tau=tz1} \quad (13\text{-}5)$$

$$= \frac{1}{2\pi}\gamma G_z^{(n)}\Delta t_z$$

$$S(k_x, k_y, k_z) = \int_{dx,dy,dz} \rho(x, y, z)\exp\left[-\frac{i}{2\pi}k_x x - \right. \quad (14)$$

$$\left. \frac{i}{2\pi}\gamma G_y^{(n)}\left\{y + \frac{v_y}{2}\Delta t_y + v_y t_{y0}\right\}\Delta t_y - \frac{1}{2\pi}\gamma G_z^{(n)}\Delta t_z\right]dx\,dy\,dz$$

$$y' = y + \frac{v_y}{2}\Delta t_y + v_y t_{y0},\ dy' = dy \quad (15)$$

$$y = y' - \frac{v_y}{2}\Delta t_y - v_y t_{y0} \quad (16)$$

-continued $$S(k_x, k_y, k_z) = \int_{dx,dy'} \rho\!\left(x, \left(y' - \frac{v_y}{2}\Delta t_y - v_y t_{y0}\right), z\right) \quad (17)$$

$$\exp\!\left[-\frac{i}{2\pi}(k_x x + \gamma G_y^{(n)} t_y y')\right]dx\,dy'\,dz$$

$$F^{-1}\{S(k_x, k_y, k_z)\} = F^{-1}\!\left\{\int_{dx,dy',dz} \rho(x, y, z)\exp\right. \quad (18)$$

$$\left[-\frac{i}{2\pi}(k_x x + \gamma G_y^{(n)} t_y y') - \right.$$

$$\left.\frac{1}{2\pi}\gamma G_z^{(n)}\Delta t_z\right]dx\,dy\,dz\Bigg\}$$

$$= \rho\!\left(x, \left(y' - \frac{v_y}{2}\Delta t_y - v_y t_{y0}\right), z\right) \quad (19)$$

$$S(k_x, k_y, k_z) = \quad (20)$$

$$\exp\!\left[-\frac{i}{2\pi}\gamma G_y^{(n)}\!\left\{\frac{v_y}{2}\Delta t_y + v_y t_{y0}\right\}\Delta t_y\right] \times \int_{dx,dy,dz}\rho(x, y, z)$$

$$\exp\!\left[-\frac{i}{2\pi}k_x x - \frac{i}{2\pi}\gamma G_y^{(n)}\Delta t_y y - \frac{1}{2\pi}\gamma G_z^{(n)}\Delta t_z\right]dx\,dy\,dz$$

$$S'(k_x, k_y, k_z) = \exp\!\left[\frac{i}{2\pi}\gamma G_y^{(n)}\!\left\{\frac{v_y}{2}\Delta t_y + v_y t_{y0}\right\}\Delta t_y\right]S(k_x, k_y, k_z) \quad (21)$$

$$F^{-1}\{S'(k_x, k_y, k_z)\} = F^{-1}\!\left\{\int_{dx,dy,dz}\rho(x, y, z)\exp\right. \quad (22)$$

$$\left[-\frac{i}{2\pi}k_x x - \frac{i}{2\pi}\gamma G_y^{(n)}\Delta t_y y - \right.$$

$$\left.\frac{1}{2\pi}\gamma G_z^{(n)}\Delta t_z\right]dx\,dy\,dz\Bigg\}$$

$$= F^{-1}\!\left\{\int_{dx,dy,dz}\rho(x, y, z)\exp\right.$$

$$\left[-\frac{i}{2\pi}(k_x x + \gamma G_y^{(n)} t_y y) - \right.$$

$$\left.\frac{1}{2\pi}\gamma G_z^{(n)}\Delta t_z\right]dx\,dy\,dz\Bigg\}$$

$$= \rho(x, y, z)$$

Thus, it is possible to obtain the corrected image signals S' ($k_x$, $k_y$, $k_z$) based on the three- or more-dimensional image signals S ($k_x$, $k_y$, $k_z$), in accordance with the equation (21). By applying Fourier transformation to the corrected image signals S' ($k_x$, $k_y$, $k_z$), it is possible to obtain accurate image signals in which the influence exerted by the movement in the direction "y" is eliminated.

The measurement device and the measurement method both in accordance with the present invention are useful as an apparatus and a method for obtaining images of an object by virtue of various magnetic resonances such as electron spin resonance and nuclear magnetic resonance. In particular, the present invention preferably provides accurate images in which the influence exerted by a moving velocity of a moving object is eliminated, in a measurement device and a measurement method for obtaining images of an object, such as functional images and morphologic images, by virtue of magnetic resonance.

While the present invention has been described in connection with certain exemplary embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The invention claimed is:

1. A measurement device for obtaining images of an object to be measured by virtue of magnetic resonance, the measurement device comprising:
an RF coil configured to keep the object therein;
a magnetic field generator for generating a static magnetic field to excite magnetic resonance of the object kept in said RF coil;
a mover for moving one of the object and said magnetic field generator to thereby move the object in the static magnetic field generated by said magnetic field generator;
a measurement unit for applying a gradient magnetic field in at least one of a moving direction "y" in which the object moves relative to said magnetic field generator, and a direction "x" perpendicular to said moving direction "y" to thereby obtain image signals of the object by virtue of at least one of phase-encoding and frequency-encoding without stopping the object or said magnetic field generator while they are being moved by said mover; and
a correction unit for eliminating influence on said image signals derived from movement of the object in said moving direction "y" to provide corrected image signals.

2. The measurement device as set forth in claim 1, wherein said correction unit provides said corrected image signals in accordance with the following equation:

$$S'(k_x, k_y) = \exp\left[\frac{i}{2\pi}\gamma G_y^{(n)}\left\{\frac{v_y}{2}\Delta t_y + v_y t_{y0}\right\}\Delta t_y\right]S(k_x, k_y)$$

wherein
S ($k_x$, $k_y$) indicates said image signals,
S' ($k_x$, $k_y$) indicates said corrected image signals,
each of $k_x$ and $k_y$ indicates a spatial frequency in said directions "x" and "y" respectively,
"$\gamma$" indicates a gyromagnetic ratio,
"$G_y^{(n)}$" indicates an intensity of a gradient magnetic field of said phase-encoding or said frequency-encoding in n-th measurement,
"$v_y$" indicates a moving velocity in the moving direction "y",
"$\Delta t_y$" indicates a period of time during which said phase-encoding or said frequency-encoding is applied, and
"$t_{y0}$" indicates a period of time until said phase-encoding or said frequency-encoding starts being applied.

3. The measurement device as set forth in claim 1, wherein said correction unit provides said corrected image signals in accordance with the following equation:

$$S'(k_x, k_y, k_z) = \exp\left[\frac{i}{2\pi}\gamma G_y^{(n)}\left\{\frac{v_y}{2}\Delta t_y + v_y t_{y0}\right\}\Delta t_y\right]S(k_x, k_y, k_z)$$

wherein
S ($k_x$, $k_y$, $k_z$) indicates said image signals,
S' ($k_x$, $k_y$, $k_z$) indicates said corrected image signals,
each of $k_x$, $k_y$ and $k_z$ indicates a spatial frequency in said direction "x", said direction "y", and a direction "z", respectively,
"$\gamma$" indicates a gyromagnetic ratio,
"$G_y^{(n)}$" indicates an intensity of a gradient magnetic field of said phase-encoding or said frequency-encoding in n-th measurement,
"$v_y$" indicates a moving velocity in the moving direction "y",
"$\Delta t_y$" indicates a period of time during which said phase-encoding or said frequency-encoding is applied, and
"$t_{y0}$" indicates a period of time until said phase-encoding or said frequency-encoding starts being applied.

4. The measurement device as set forth in claim 1, wherein said magnetic field generator includes a first magnetic field generator for generating a first static magnetic field having a predetermined intensity, and a second magnetic field generator for generating a second static magnetic field having an intensity different from said intensity of said first static magnetic field, and
said mover moves one of the object, said first magnetic field generator, and said second magnetic field generator to thereby move the object through static magnetic fields generated by said first magnetic field generator and said second magnetic field generator in this order.

5. The measurement device as set forth in claim 4, wherein said mover comprises a rotator which rotates one of the object and said first and second magnetic field generators to thereby move the object through static magnetic fields generated by said first magnetic field generator and said second magnetic field generator in this order.

6. The measurement device as set forth in claim 4, wherein one of said first and second magnetic field generators excites nuclear magnetic resonance for measurement, and the other excites electron spin resonance for measurement.

7. The measurement device as set forth in claim 2, wherein said magnetic field generator includes a first magnetic field generator for generating a first static magnetic field having a predetermined intensity, and a second magnetic field generator for generating a second static magnetic field having an intensity different from said intensity of said first static magnetic field, and
said mover moves one of the object, said first magnetic field generator, and said second magnetic field generator to thereby move the object through static magnetic fields generated by said first magnetic field generator and said second magnetic field generator in this order.

8. The measurement device as set forth in claim 2, wherein said mover comprises a rotator which rotates one of the object and said first and second magnetic field generators to thereby move the object through static magnetic fields generated by said first magnetic field generator and said second magnetic field generator in this order.

9. The measurement device as set forth in claim 7, wherein one of said first and second magnetic field generators excites nuclear magnetic resonance for measurement, and the other excites electron spin resonance for measurement.

10. The measurement device as set forth in claim 3, wherein said magnetic field generator includes a first magnetic field generator for generating a first static magnetic field having a predetermined intensity, and a second magnetic field generator for generating a second static magnetic field having an intensity different from said intensity of said first magnetic field generator, and
said mover moves one of the object, said first magnetic field generator, and said second magnetic field generator to thereby move the object through magnetic fields generated by said first magnetic field generator and said second magnetic field generator in this order.

11. The measurement device as set forth in claim 3, wherein said mover comprises a rotator which rotates one of the object and said first and second magnetic field generators to thereby move the object through static magnetic fields generated by said first magnetic field generator and said second magnetic field generator in this order.

12. The measurement device as set forth in claim 10, wherein one of said first and second magnetic field generators excites nuclear magnetic resonance for measurement, and the other excites electron spin resonance for measurement.

13. A measurement method for obtaining images of an object to be measured by virtue of magnetic resonance, the method comprising:

moving one of the object kept in an RF coil and a magnetic field generator which generates a static magnetic field to excite magnetic resonance of the object to thereby move the object through the static magnetic field generated by said magnetic field generator;

applying a gradient magnetic field in at least one of a moving direction "y" in which the object moves relative to said magnetic field generator, and a direction "x" perpendicular to said moving direction "y" to thereby obtain image signals of the object by virtue of at least one of phase-encoding and frequency-encoding without stopping the object or said magnetic field generator while they are being moved; and eliminating influence on said image signals derived from movement of the object in said moving direction "y" to provide corrected image signals.

14. The measurement method as set forth in claim 13, wherein said corrected image signals are calculated in accordance with the following equation:

$$S'(k_x, k_y) = \exp\left[\frac{i}{2\pi}\gamma G_y^{(n)}\left\{\frac{v_y}{2}\Delta t_y + v_y t_{y0}\right\}\Delta t_y\right]S(k_x, k_y)$$

wherein $S(k_x, k_y)$ indicates said image signals, $S'(k_x, k_y)$ indicates said corrected image signals, each of $k_x$ and $k_y$ indicates a spatial frequency in said directions "x" and "y" respectively, "$\gamma$" indicates a gyromagnetic ratio, "$G_y^{(n)}$" indicates an intensity of a gradient magnetic field of said phase-encoding or said frequency-encoding in n-th measurement, "$v_y$" indicates a moving velocity in the moving direction "y", "$\Delta t_y$" indicates a period of time during which said phase-encoding or said frequency-encoding is applied, and "$t_{y0}$" indicates a period of time until said phase-encoding or said frequency-encoding starts being applied.

15. The measurement method as set forth in claim 13, wherein said corrected image signals are calculated in accordance with the following equation:

$$S'(k_x, k_y, k_z) = \exp\left[\frac{i}{2\pi}\gamma G_y^{(n)}\left\{\frac{v_y}{2}\Delta t_y + v_y t_{y0}\right\}\Delta t_y\right]S(k_x, k_y, k_z)$$

wherein $S(k_x, k_y, k_z)$ indicates said image signals, $S'(k_x, k_y, k_z)$ indicates said corrected image signals, each of $k_x$, $k_y$ and $k_z$ indicates a spatial frequency in said direction "x", said direction "y", and a direction "z", respectively, "$\gamma$" indicates a gyromagnetic ratio, "$G_y^{(n)}$" indicates an intensity of a gradient magnetic field of said phase-encoding or said frequency-encoding in n-th measurement, "$v_y$" indicates a moving velocity in the moving direction "y", "$\Delta t_y$" indicates a period of time during which said phase-encoding or said frequency-encoding is applied, and "$t_{y0}$" indicates a period of time until said phase-encoding or said frequency-encoding starts being applied.

16. The measurement method as set forth in claim 13, wherein the object is caused to rotate while the object is being moved through said static magnetic field.

17. The measurement method as set forth in claim 13, wherein the object is caused to pass through two static magnetic fields one of which excites nuclear magnetic resonance, and the other excites electron spin resonance.

* * * * *